United States Patent
Ehlert

(10) Patent No.: US 10,918,643 B2
(45) Date of Patent: Feb. 16, 2021

(54) NO-DONORS FOR THE TREATMENT OF CEREBROVASCULAR VASOSPASMS AFTER BRAIN HEMORRHAGE

(71) Applicant: Westfaelische Wilhelms-Universitaet Muenster, Muenster (DE)

(72) Inventor: Angelika Ehlert, Hamburg (DE)

(73) Assignee: Westfaelische Wilhelms-Universitaet Muenster, Muenster (DE)

( * ) Notice: Subject to any disclaimer, the term of this patent is extended or adjusted under 35 U.S.C. 154(b) by 64 days.

(21) Appl. No.: 15/760,992

(22) PCT Filed: Sep. 16, 2016

(86) PCT No.: PCT/EP2016/071932
§ 371 (c)(1),
(2) Date: Mar. 16, 2018

(87) PCT Pub. No.: WO2017/046304
PCT Pub. Date: Mar. 23, 2017

(65) Prior Publication Data
US 2018/0243314 A1 Aug. 30, 2018

(30) Foreign Application Priority Data
Sep. 16, 2015 (EP) .................................... 15185479

(51) Int. Cl.
*A61K 31/5377* (2006.01)
*A61K 31/295* (2006.01)
*A61K 33/26* (2006.01)
*A61K 31/4245* (2006.01)
*A61K 45/06* (2006.01)

(52) U.S. Cl.
CPC ........ *A61K 31/5377* (2013.01); *A61K 31/295* (2013.01); *A61K 31/4245* (2013.01); *A61K 33/26* (2013.01); *A61K 45/06* (2013.01)

(58) Field of Classification Search
None
See application file for complete search history.

(56) References Cited

FOREIGN PATENT DOCUMENTS

| EP | 2764868 A1 | 8/2014 |
|---|---|---|
| WO | 2012/069620 A1 | 5/2012 |

OTHER PUBLICATIONS

Kumar et al.("Intraventricular sodium nitroprusside therapy: A future promise for refractory subarachnoid hemorrhage-induced vasospasm", Neurology India, 2003, vol. 51(2), pp. 197-202.*
Ehlert, A., et al. (2016) "A Case of Hyperacute Onset of Vasospasm After Aneurysmal Subarachnoid Hemorrhage and Refractory Vasospasm Treated with Intravenous and Intraventricular Nitric Oxide: A Mini Review", World Neurosurgery, 91:673.
Ehlert, A., et al. (2015) "Molsidomine for the prevention of vasospasm-related delayed ischemic neurological deficits and delayed brain infarction and the improvement of clinical outcomeafter subarachnoid hemorrhage: a single-center clinical observational study", Journal of Neurosurgery, 124:51-58.
Ehlert, A., et al. (2011) "Molsidome treatment for the prophylaxis of DIND and delayed brain infarction following subarachnoid hemorrhage", German Society of Neurosurgery, 62nd Annual Meeting of the German Society of Neurosurgery, Abstract.
Raabe, A., et al. (2002) "Effect of Intraventricular Sodium Nitroprusside on Cerebral Hemodynamics and Oxygenation in Poor-grade Aneurysm Patients with Severe, Medically Refractory Vasospasm", Neurosurgery, 50:1006-1014.
Vajkoczy, P., et al. (2000) "Intrathecal Sodium Nitroprusside Improves Cerebral Blood Flow and Oxygenation in Refractory Cerebral Vasospasm and Ischemia in Humans", Stroke 31:1195-1198.
Hanggi, D., and Steiger, H.-J. (2006) "Nitric oxide in subarachnoid haemorrhage and its therapeutics implications", Acta Neurochirurgica 148:605-613.
Zhang, F., and Iadecola, C. (1994) "Reduction of Focal Cerebral Ischemic Damage by Delayed Treatment With Nitric Oxide Donors", Journal of Cerebral Blood Flow and Metatabolism 14:574-580.
Yamamoto, S., et al. (1997) "Subarachnoid hemorrhage impairs cerebral blood flow response to nitric oxide but not to cyclic GMP in large cerebral arteries", Brain Research 757:1-9.
Zhang, F., et al. (1994) "Nitric Oxide Donors Increase Blood Flow and Reduce Brain Damage in Focal Ischemia: Evidence that Nitric Oxide is Beneficial in the Early Stages of Cerebral Ischemia", Journal of Cerebral Blood Flow and Metabolism 14:217-226.

* cited by examiner

Primary Examiner — Savitha M Rao
Assistant Examiner — Gregg Polansky
(74) Attorney, Agent, or Firm — Kagan Binder, PLLC

(57) ABSTRACT

The present invention relates to the combined use of NO-donors for the treatment, prevention and/or amelioration of disturbances of the cerebral macro- and microcirculation which disturbances cause cerebrovascular spasms (CVS) and/or malperfusion of brain parenchyma caused by blood vessel and blood flow dysregulation.

18 Claims, 4 Drawing Sheets

NO-DONORS FOR THE TREATMENT OF CEREBROVASCULAR VASOSPASMS AFTER BRAIN HEMORRHAGE

CROSS REFERENCE TO RELATED APPLICATIONS

Figure 1:
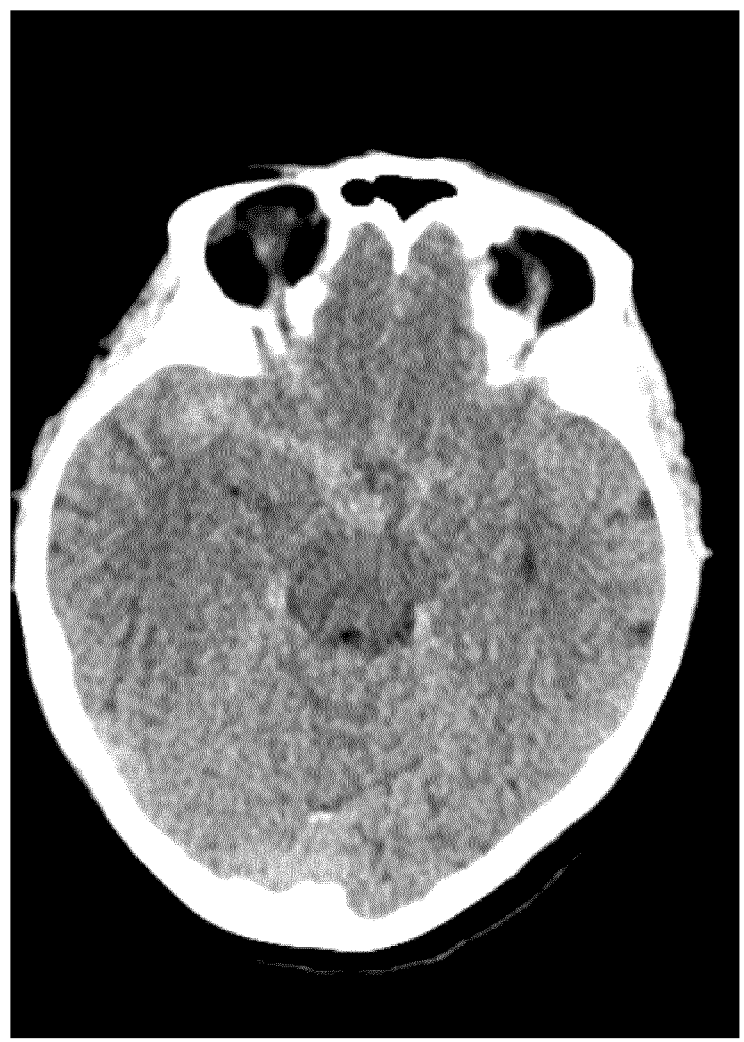

This application claims priority to International Application No. PCT/EP2016/071932, filed on Sep. 16, 2016, which claims the benefit of foreign Application No. EP 15185479.1, filed Sep. 16, 2015, said applications which are incorporated herein by reference.

About 50% of patients suffering from brain hemorrhage, such as subarachnoid haemorrhage (SAH) develop delayed ischemic neurological deficits (DINDs) or delayed cerebral infarctions and persistent neurological deficits (DCI). Even a "good" outcome is associated with persistent intellectual deficits in approximately 75% of patients. Those quite dismal numbers are significantly worse in patients who are admitted with early vasospasm and/or poor clinical status.

After the introduction of nimodipine in 1983, no reliable new therapeutic approach for vasospasm and vasospasm-associated DCI after SAH has been developed. Only orally administered nimodipine has been proven to decrease the likelihood of DCI and poor clinical outcome (Macdonald, Neurosurg Rev 29:179-193, 2006). Nonetheless, despite nimodipine vasospasm-generated infarcts occur in 20-50%, DCIs in 27-37%, and severe morbidity in 30-40% of patients (Frontera et al., Stroke 40:1963-1968, 2009). In case of evolving DCI a favorable outcome will take place in less than 10%, whereas the majority of those patients (62%) has a very poor outcome (Frontera et al., J Neurol Neurosurg Psychiatry. 2015; 86:71-78).

The widely used 3H therapy (Dorsch, Brit J Neurosurg. 1995; 9:403-412) has also been criticized recently and if used it has become rather 1 or 2H than 3H therapy (predominantly induced hypertension). Furthermore, even powerful suppression of (measurable) vasospasms by Clazosentan does not lead to an improved outcome (Macdonald et al., Nat Clin Pract Neurol. 2007; 3:256-263). Other treatments like fasudil (Suzuki et al., Surg Neurol. 2007; 68:126-131) or anti-inflammatory agents (Muroi et al., Neurocrit Care. 2014; 20:240-246) did not achieve a wider acceptance either.

Arteriographic vasospasm is detected in approximately 60%-70% of patients after SAH, but not all of them develop DINDs, possibly because of a sufficient collateral blood supply. On the other hand, cerebral vasospasm (CVS), as detected by transcranial Doppler (TCD) ultrasonography or arteriography, is not present in every patient with DINDs. In these cases, DINDs have been attributed to decreased blood flow through the microcirculation due to a locally reduced availability of nitric oxide (NO). Thus, detectable CVS in the macrocirculation may facilitate the development of DINDs but is not necessarily its main cause. These findings suggest that the impact of cerebral microcirculation on the development of DINDs and poor outcome has been underestimated.

Recently, this concept was further supported by results of the CONSCIOUS 1-3 trials, which treated CVS patients with endothelin receptor antagonists, and a newly published randomized trial investigating the therapeutic effect of cilostazol, an inhibitor of phosphodiesterase 3. TCD ultrasonography-detectable vasospasm was significantly reduced, but the rate of DINDs and related infarcts showed only a statistical trend toward improvement, and the clinical outcome was not altered, possibly because clazosentan acted only on the large conductive cerebral arteries.

For years, many treatments of DINDs and CVS after SAH have been tried, including compounds with improved NO delivery. Several of them showed beneficial effects on CVS, DIND, or clinical outcome. Unfortunately, some NO-delivering drugs and their administration routes have been associated with side effects such as systemic hypotension or cyanide toxicity. An alternative NO donor with more favorable pharmacodynamic and pharmacokinetic profiles and less toxicity is molsidomine, a standard treatment for heart failure and coronary heart disease. Recently, it was demonstrated that patients suffering from SAH who were treated with intravenous molsidomine had a significant improvement in clinical outcome and less cerebral infarction (Ehlert et al., 2015; DOI: 10.3171/2014.12.JNS13846). However, there is still a need for the treatment of cerebrovascular vasospasms after brain hemorrhage.

The technical problem underlying the present invention is to comply with the need for a treatment of cerebrovascular vasospasms after brain hemorrhage. The solution—the use of a NO donor prodrug which has to be metabolized by a subject and an active NO-delivering NO donor which is administered intracranially to said subject—is reflected in the claims, the description and the examples and illustrated in the figures.

The present inventor applied a rescue therapy scheme using a NO donor prodrug which has to be metabolized by a subject and an active NO delivering NO donor via intracranial, particularly intraventricular application and observed surprisingly, that such combined NO-donors seem to exert a synergistic impact by potentiation of each other leading to an improvement of the recently reported emergency therapy (Ehlert et al., loc. cit.) applying only a NO donor prodrug which has to be metabolized by a subject. The NO donor prodrug which has to be metabolized by a subject is preferably administered intravenously, intraarterially or intravascularly. It is preferably continuously administered. The active NO-delivering NO donor is preferably administered intracranially, such as intrathecally, intracisternally, intraventricularly, or submeningeally or it is preferably administered intraarterially.

From what the present inventor observed, it seems that the permanent presence of a NO donor prodrug which has to be metabolized by a subject prevents a NO sink effect and preserves the susceptibility of brain vessels to additional exposure of NO by an active NO delivering NO donor, which led to powerful efficacy when an active NO-delivering NO donor is administered intracranially.

Accordingly, contrary to former reports on intracranial application of an active NO-delivering NO donor, the present inventor achieved homogenous effects exerted by an intracranially administered active NO-delivering NO donor, most likely due to the fact that a continuously administered NO donor prodrug which has to be metabolized by a subject provided a permanent level of NO in the brain, while an intracranially administered active NO-delivering NO donor is believed to bolster the NO supply in the brain.

In particular, the present inventor addressed the use of NO donors to treat a severe clinical course of vasospasm after SAH in a 65-year old woman admitted within 1 hour after aneurismal SAH (Hunt&Hess grade III, Fisher modified by Frontera—grade IV) with arteriographically confirmed hyperacute vasospasm. A right main cerebral artery (MCA) aneurysm was immediately coiled and the patient was placed on standard anti-vasospastic therapy. Within 48 hours after aneurysm repair the patient developed cerebral vasospasms with clinical deterioration (delayed cerebral ischemia; DCI). Since the standard therapy failed to control clinical symptoms of DCI and to address severe vasospasm, an individualized rescue treatment with nitric oxide (NO) donors was initiated. A NO donor which has to be metabolized, particularly Molsidomine was given and clinical stabilization had been achieved for a week (Hunt&Hess grade I, WFNS I) when vasospasm and DCI progressed. During this DCI (somnolence and coma, left-sided hemiplegia with neglect, aphasia, right-sided hemiparesis) the present inventor escalated NO donor therapy by adding intracranially, particularly intraventricular boluses of an active NO-delivering NO donor, particularly sodium nitroprusside (SNP). Over the course of 22 days 7 transient clinical deteriorations were treated with boluses of said active NO-delivering NO donor during continuous therapy with a NO donor prodrug which has to be metabolized and each time vasospasm and DCI were completely resolved. Despite severe complications of aneurismal SAH that usually result in a poor outcome, the clinical outcome of this patient was excellent. At 3, 6, and 12 months follow up her mNIH-SS and mRS were 0 and she did not have any cognitive deficit. This demonstrates that the use of a NO donor prodrug which has to be metabolized and the use of an active NO-delivering NO donor that is administered intracranially are beneficial in the treatment, prevention and/or amelioration of disturbances of the cerebral macro- and microcirculation which disturbances cause cerebrovascular spasms (CVS) and/or malperfusion of brain parenchyma caused by blood vessel and blood flow dysregulation.

Accordingly, the present invention relates (i) to a nitric oxide (NO) donor for use in a method of treatment, prevention and/or amelioration of disturbances of the cerebral macro- and microcirculation which disturbances cause cerebrovascular spasms (CVS) and/or malperfusion of brain parenchyma caused by blood vessel and blood flow dysregulation, said method comprising administering to the subject a NO donor prodrug which has to be metabolized by said subject into the active NO-delivering form and intracranially administering an active NO-delivering NO donor.

The present invention also relates (ii) to an active NO-delivering nitric oxide (NO) donor for use in a method of treatment, prevention and/or amelioration of disturbances of the cerebral macro- and microcirculation which disturbances cause cerebrovascular spasms (CVS) and/or malperfusion of brain parenchyma caused by blood vessel and blood flow dysregulation in a subject, wherein the subject is subject to therapy with an NO donor prodrug which has to be metabolized by said subject into the active NO-delivering form.

Furthermore, the present invention (iii) provides a NO donor prodrug which has to be metabolized in a subject into the active NO-delivering form for use in a method of treatment, prevention and/or amelioration of disturbances of the cerebral macro- and microcirculation which disturbances cause cerebrovascular spasms (CVS) and/or malperfusion of brain parenchyma caused by blood vessel and blood flow dysregulation in a subject, wherein the subject is subject to therapy with an active NO-delivering nitric oxide (NO) donor.

The present invention moreover (iv) provides a dosage regime for use in a method of treatment, prevention and/or amelioration of disturbances of the cerebral macro- and microcirculation which disturbances cause cerebrovascular spasms (CVS) and/or malperfusion of brain parenchyma caused by blood vessel and blood flow dysregulation, comprising (a) continuously administering a NO donor prodrug which has to be metabolized as defined herein intravenously, intraarterially or intravascularly prior to, concurrently and/or after NO deficiency-induced disturbances of the cerebral macro- and microcirculation such that the mean arterial pressure (MAP) is maintained at at least 65 mm Hg; and
(b) administering an active NO-delivering NO donor as defined herein intracranially.

The present invention further (v) provides a kit comprising Molsidomine and Nitroprusside, optionally further comprising Nimodipine and/or Clazosentan.

Preferred embodiments of (i) to (v) as described above and mirrored in the claims are described in the claims.

A "nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo and/or are oxidized to produce nitric oxide and/or are substrates for nitric oxide synthase and/or cytochrome P450. "NO donor" also includes compounds that are precursors of L-arginine, inhibitors of the enzyme arginase and nitric oxide mediators. NO is an important messenger molecule involved in many pathological and physiological processes within the mammalian body. Exogenous NO sources constitute a powerful way to supplement NO when the body cannot generate enough for normal biological functions.

An NO donor prodrug of the present invention can provide NO when said NO donor prodrug has been metabolized by a subject, to whom said NO donor prodrug is administered, into the active NO-delivering form. "Metabolized" is thereby preferably hepatoselective, i.e. metabolized by the liver. NO donor prodrugs of the present invention include but are not limited to those mentioned in the claims. Molsidomine is thereby particularly preferred.

An active NO donor of the present invention can actively deliver NO, i.e., it does not need to be metabolized into the NO-delivering form, but is already in a NO-delivering form in which it actively releases NO. Active release of NO includes spontaneous release. Active release of NO may occur through break down of the NO-donor or by ligand-exchange. Active NO donor prodrugs of the present invention include but are not limited to those mentioned in the claims. Nitroprusside is thereby particularly preferred.

A most preferred combination within the gist of the present invention is Molsidomine (NO donor prodrug) with Nitroprussid (active NO donor). It is even more preferred that Molsidomine is administered intravenously, intraarterially or intravascularly, intravenously being preferred and Nitroprussid is administered intercranially, intraventricularly being preferred.

It is preferred that the above mentioned combinations of compounds (NO donor prodrug and active NO donor) is administered in a dose range from 1 mg/hour to 16 mg/hour NO donor prodrug (preferably Molsidomine) and 2-5 mg/hour, preferably 3 mg/hour active NO donor (preferably Nitroprussid).

As described herein, microcirculation is the flow of blood cells and blood plasma in the smallest blood vessels having diameters of less than 200 µm. Microcirculation is functionally the most important part of blood circulation because here exchange of substances with the cells of the tissue is realized. This applies to the transportation of oxygen and substrates to the cells as wells as the transportation of metabolic end products away from the cells and the tissue.

The specific functional state of microcirculation determines the required regulation with respect to an adaptation of microperfusion towards changing metabolic needs. Furthermore, undisturbed microcirculation is the prerequisite for non-restricted processing of the first steps of an immunological reaction. Here, the local regulation of microcirculation, specifically the autoregulation of brain resistance vessels and auto-rhythmic contraction of vascular smooth muscle cells are of particular importance.

Amongst others, important criteria for characterizing normal or impaired microcirculation are:
- the particular distribution state of the blood in the microvessel network;
- auto-rhythmic (spontaneous) vessel agitation in arterioles and venules (vasomotion);
- flow in arteriolar inflow and venular flow-off;
- rheologic features (local hematocrit);
- flow velocity of blood cells;
- diameter of micro-vessels.

The vaso-motoric functional state determines essentially the width of adjustment of microcirculation to changing metabolic needs and, therefore, the local width of regulation of microcirculation.

The person skilled in the art is in the position to obtain measurement data of blood microcirculation, said measurement data comprising features like the exhaustion of oxygen in the venules, blood flow in the venules, local hematocrit in the micro-vessels, spontaneous arteriolar vasomotion, state of vasomotion in the venules, and local changes in concentration of substances in tissue. A further explanation of these features is given at pages 5 and 6 of international patent application WO 2008/025731 A1, which describes non-invasive measuring methods on a target tissue in order to describe the aforementioned features of the microcirculation of the blood, while otherwise mainly relating to a device for generating a pulsed electromagnetic field with pulse control for improving microcirculation of the blood. The said explanations of the above-mentioned features given in WO 2008/025731 is specifically referred to herewith and, therefore, the corresponding disclosure of WO 2008/025731 A1 forms part of the present application. Furthermore, WO 2008/025731 A1 also includes at pages 6/7 a reference to the literature with respect to the basics for measurement of these features. By way of reference, this disclosure of WO 2008/025731 also forms part of the present application herewith.

Disturbances of the cerebral macro and microcirculation may be induced or caused by NO deficiency. It is assumed that the NO deficiency occurs after, for example, an aneurismal SAH because of a NO sink-effect. It is assumed that hemoglobin and its degradation products (oxy-hemoglobin, metabolites of the hemoglobin) of the blood/blood clot attached to the cerebral vessels after brain hemorrhage, in particular after SAH, play a decisive, pluripotent role in spasm, without being bound by theory, mostly by counteracting NO together with destroying NOS and/or by generating free oxygen specimen, lipid peroxidation, inflammation, inducing synthesis of vasoconstrictors and destruction of vessel wall and mechanical subjecting cerebral vessels to pressure. Indeed, the most important vasodilator of cerebral arteries is NO, produced in the healthy endothelium of vessels by (inter alia) constitutive synthases in a continuous basal manner. In addition, NO is produced by neurons, glia, endothelium and perivascular parasympathetic nerve fibers, the latter mainly originate from sphenopalatine ganglion and vascular smooth muscle cells either constitutively or after stimulation. Apart from endothelium-derived NO, astrocyte- and neuron-released NO contributes to the control of cerebral blood vessels function and cortical blood flow. In summary, relaxations of large cerebral arteries, resistance vessels and small cerebral arteries and, thus, consequently the control the cortical blood flow and supply, are strictly dependent on the presence of NO. A lack of the basal NO-availability would cause a vasoconstriction due to elevated levels of endothelin and rho-kinase and due to the underlying basic myogenic tone of cerebral arteries. After, in particular SAH, a significant decrease up to total disappearance of endothelial NOS and related mRNA in great and small cerebral arteries is proven, leading to impaired vasodilatation.

In various embodiments, the NO deficiency-induced disturbances of the cerebral microcirculation and/or macrocirculation cause cerebral vasospasms (can be equally used herein with the term "cerebrovascular spasms") (CVS) and/or malperfusion of brain parenchyma caused by blood vessel and/or blood flow dysregulation. In various embodiments, said cerebral vasospasms cause secondary neurological deficiencies (DIND) and/or delayed cerebral infarctions and persistent neurological deficits (DCI) and/or brain infarction.

While intracerebral hemorrhage (ICH) is bleeding directly into the brain tissue, forming a gradually enlarging hematoma (pooling of blood), intracranial hemorrhage is the accumulation of blood anywhere within the skull vault. In the present invention, the NO deficiency-induced disturbances of the cerebral microcirculation and/or macrocirculation are preferably NO deficiency-induced disturbances of the cerebral microcirculation and/or macrocirculation due to an intracranial hemorrhage or stroke. An outstanding aspect is a therapeutic preconditioning and a resulting improved ischaemia tolerance of brain at risc by nitroxide (for example perioperatively). The result of such a pre-conditioning is a better cytoprotection, angio- and neuro-neogenesis (86). NO contributes to a limitation of infarction volumes and an improvement of the outcome after infarction. This is finally done based on an improvement of the CBF after preconditioning by NO, scavenging of free oxygen species, inhibition of caspase-3, the anti-inflammatory and anti-thrombotic characteristics, but also a stimulation of growth factors and proteins such as VEGF and phosphoinositide 3-kinase, which stops the neuronal apoptosis at least in the penumbra. Nitroxide limits the damage due to cortical spreading (87-91), stops the transport of excitatory amino acids transporters through cell membranes (92) and inhibits the immunological response and activation of microglia triggered by ischemic events—phagocytosis and secretion of chemo- and cytokines by microglia (93,94). Accordingly, as mentioned above, the present invention also envisages that an NO donor is administered to a subject prior to any measure such as brain surgery that may cause nitric oxide deficiency-induced disturbances of the cerebral microcirculation of a human subject.

In various embodiments, said intracranial hemorrhage results from a traumatic or a non-traumatic cause.

A distinction is made between intra-axial hemorrhage (blood inside the brain) and extra-axial hemorrhage (blood inside the skull but outside the brain). Intra-axial hemorrhage is due to intra-parenchymal hemorrhage or intraventricular hemorrhage (blood in the ventricular system). In the present invention, the NO deficiency-induced disturbances of the cerebral microcirculation and/or macrocirculation due to an intracranial hemorrhage are preferably NO deficiency-induced disturbances of the cerebral microcirculation and/or macrocirculation due to an intra-axial hemorrhage (cerebral hemorrhage) or an extra-axial hemorrhage.

Preferably, said intra-axial hemorrhage is an intraparenchymal hemorrhage, an intraventricular hemorrhage, or intraventricular traumatic diffuse bleeding. In various embodiments, said intra-axial hemorrhage and extra-axial hemorrhage result from a traumatic or a non-traumatic cause.

Likewise, in various embodiments said intraparenchymal hemorrhage, intraventricular hemorrhage, and intraventricular traumatic diffuse bleeding result from a traumatic or a non-traumatic cause.

In various embodiments, the intra-axial hemorrhage is caused by brain trauma, hemorrhagic stroke and/or spontaneous bleeding into the brain. Likewise, in various embodiments the intraparenchymal hemorrhage, intraventricular hemorrhage, or intraventricular traumatic diffuse bleeding is caused by brain trauma, hemorrhagic stroke and/or spontaneous bleeding into the brain.

The main types of extra-axial hemorrhage are epidural hematoma (bleeding between the dura mater and the skull), subdural hematoma (in the subdural space) and subarachnoid hemorrhage (SAH) (between the arachnoid mater and pia mater). In the present invention, the extra-axial hemorrhage is preferably extra-axial chronical response acute and/or sub-acute bleeding. In various embodiments, the extra-axial hemorrhage according to the present invention is an epidural, subdural or subarachnoid hemorrhage (SAH). Therefore, in various embodiments the NO deficiency-induced disturbances of the cerebral microcirculation and/or macrocirculation are preferably NO deficiency-induced disturbances of the cerebral microcirculation and/or macrocirculation due to an epidural hemorrhage, subdural hemorrhage (such as chronic subdural hemorrhage) or subarachnoid hemorrhage (SAH). Similarly, NO deficiency-induced disturbances of the cerebral microcirculation and/or macrocirculation are preferably NO deficiency-induced disturbances of the cerebral microcirculation and/or macrocirculation due to irritation of the brain surface due to, for example, surgical methods such as tumor resection, by-pass operation or revascularization by myosangiosis at the brain or post-operative hemorrhage in the brain. More preferably, in the present invention the NO deficiency-induced disturbances of the cerebral microcirculation and/or macrocirculation are preferably NO deficiency-induced disturbances of the cerebral microcirculation and/or macrocirculation due to delayed cerebral vasospasm (DCV) and delayed ischemic neurological deficit (DIND) after SAH. For the latter preferred embodiment, Molsidomine is most preferably applied.

In various embodiments, the extra-axial hemorrhage according to the present invention results from a non-traumatic or traumatic cause. More preferably, the extra-axial hemorrhage according to the present invention is caused by an aneurysm or a head trauma (head injury).

Likewise, in various embodiments the epidural, subdural or subarachnoid hemorrhage according to the present invention results from a non-traumatic or traumatic cause. More preferably, in various embodiments the epidural, subdural or subarachnoid hemorrhage according to the present invention is caused by an aneurysm or a head trauma (head injury). In various embodiments, the extra-axial hemorrhage according to the present invention is spontaneous, preferably spontaneous due to an aneurysm. Likewise, in various embodiments the epidural, subdural or subarachnoid hemorrhage according to the present invention is spontaneous, preferably spontaneous due to an aneurysm.

In various embodiments, DCV after SAH according to the present invention results from a non-traumatic or a traumatic cause. More preferably, DCV after SAH according to the present invention is caused by an aneurysm or head trauma (head injury). In various embodiments, DCV after SAH according to the present invention is spontaneous, preferably spontaneous due to an aneurysm.

As described herein, in various embodiments intracranial hemorrhage is preferably an extra-axial hemorrhage. Preferably, the extra-axial hemorrhage is an extra-axial chronical response acute bleeding. In various embodiments, the extra-axial hemorrhage is preferably an epidural hemorrhage, a subdural hemorrhage or a subarachnoid hemorrhage. In various preferred embodiments, the extra-axial hemorrhage as described herein is caused by an aneurysm or trauma (head trauma).

In various embodiments, the NO donor prodrug and/or active NO donor is administered to a human subject in need thereof prior to, concurrently and/or after occurrence of NO deficiency-induced disturbances of the cerebral microcirculation and/or macrocirculation according to the present invention.

In the present invention, the human subject suffering from a NO deficiency-induced disturbance of the cerebral microcirculation and/or macrocirculation according to the present invention may also be considered as a patient suffering from a NO deficiency-induced disturbance of the cerebral microcirculation and/or macrocirculation according to the present invention. In various embodiments, a patient in need of a treatment with a NO donor according to the present invention may be a patient that had received a treatment for treating, preventing and/or ameliorating a NO deficiency-induced disturbance of the cerebral macrocirculation prior to a treatment, prevention or amelioration of a NO deficiency-induced disturbance of the cerebral microcirculation according to the present invention.

In various embodiments, the human subject in need of a NO donor according to the present invention is tested prior to administration of the NO donor in order to determine the extent of impairment of the NO deficiency-induced cerebral microcirculation. Cerebral microcirculation and macrocirculation can be visualized by the skilled person using standard means available in the art, for example, orthogonal polarization spectral (OPS) imaging. The microvascular network may be visualized using an SDF videomicroscopy system (MicroScan™, MicroVisionMedical Inc., Amsterdam, Netherlands) or a blood flow measuring probe or metabolic measuring probe, by electrocorticography, microscopically, or the like.

In various embodiments, the human subject according to the present invention is a human subject that has survived an intracranial hemorrhage or stroke according to the present invention. Preferably, said human subject that has survived an intracranial hemorrhage or stroke according to the present invention is a human subject that has survived a delayed cerebral vasospasm (DCV) after an intracranial hemorrhage or stroke according to the present invention. More preferably, said human subject that has survived a DCV according to the present invention is a human subject that has survived a DCV after a SAH according to the present invention.

In various embodiments, the human subject in need of a NO donor according to the present invention is a human subject that has survived a brain infarction and/or a secondary neurological deficiency (DIND) according to the present invention. Preferably, the human subject in need of a NO donor according to the present invention is a human subject that has survived a brain infarction and/or a DIND post a DCV, wherein the DCV preferably is a DCV after an intracranial hemorrhage or stroke according to the present invention, and wherein said intracranial hemorrhage preferably is a SAH.

In various other embodiments, the human subject is already treated with Nimodipine and/or Clazosentan, i.e., Nimodipine and/or Clazosentan is or has been administered to said human subject. In this embodiment, an NO donor, in particular an NO donor as described herein, is then also administered, i.e., an NO donor and Nimodipine and/or Clazosentan are administered in combination or applied in the form of a co-therapy.

As described herein, the human subject in need of administration of a NO donor according to the present invention (i.e., a "human subject in need thereof", as described herein) is a human subject suffering from a NO deficiency-induced disturbance of the cerebral microcirculation and/or macrocirculation in accordance with the present invention. In other words, the "human subject in need thereof" is a human subject suffering from a NO deficiency-induced disturbance of the cerebral microcirculation and/or macrocirculation as described herein, and said subject is thus in need of a NO donor in accordance with the present invention, i.e. a NO donor useful in the treatment, prevention and/or amelioration of NO deficiency-induced disturbances of the cerebral microcirculation and/or macrocirculation in a human subject.

In NO deficiency-induced disturbances of the cerebral microcirculation, there is a primary tissue impairment followed by a secondary impairment of the affected tissue, which is, for example, due to inflammation occurring after a human subject had suffered a NO deficiency-induced disturbances of the cerebral microcirculation. In various embodiments, the NO donor according to the present invention provides for an inhibition of said secondary inflammation-based impairment of the affected tissue. As the secondary inflammation-based impairment of the tissue affected by a NO deficiency-induced disturbance of the cerebral microcirculation may be the cause of secondary neurological deficiencies (DIND) according to the present invention, a NO donor according to the present invention is useful in the treatment, prevention and/or amelioration of such DINDs according to the present invention. As the DINDs according to the present invention may be causative for morbidity and/or mortality of a human subject suffering from a NO deficiency-induced disturbance of the cerebral microcirculation, a NO donor according to the present invention is useful for the prevention of morbidity and/or mortality of a human subject suffering from a NO deficiency-induced disturbance of the cerebral microcirculation.

More preferably, a NO donor prodrug according to the present invention is a compound having the following formula I or a pharmaceutically acceptable salt of said compound:

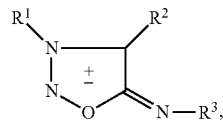

wherein $R^1$ is morpholine, N-heterocyclyl or $N(R^4)_2$, $R^2$ is H, alkyl, halogen, alkenyl, alkynyl, aryl, aralkyl, aralkenyl, alkylene, alkenylene, cycloalkyl, cycloalkylene or N-heterocyclyl, $R^3$ is H, —NO, —SO$_2$R$^4$, —C(O)OR$^4$, —C(O)R$^4$, —CH$_2$NHC(O)R$^4$, —CHR$^4$, —NR$^4$, —CHR$^4$OC(O)R$^4$ and —C(O)CHR$^4$N$^+$H$_2$, and each $R^4$ is independently hydrogen, alkyl, alkenyl, alkynyl, aryl, aralkyl or aralkenyl. Preferably, in the compound according to the above formula I $R^1$ is morpholine, $R^2$ is H and $R^3$ is —C(O)OC$_2$H$_5$.

Still more preferably, the NO donor prodrug to be used in the present invention is N-ethoxycarbonyl-3-morpholinosydnonimine (molsidomine). Molsidomine to be used in the present invention is marketed in Germany under the trademark name Corvaton®, and has the following formula II

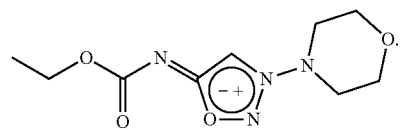

A preferred form of molsidomine to be used in the present invention is 3-morpholinosydnonimine (SIN-1). SIN-1 has the following formula III

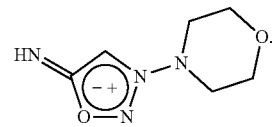

Accordingly, SIN-1 is a preferred NO donor to be used in the present invention.

In other preferred embodiments, in the compound according to the above formula I $R^1$ is morpholine, $R^2$ is H and $R^3$ is H.

In still further preferred embodiments, the NO donor prodrug according to formula I is at least one of 3-(3,3-dimethyl-1-oxo-1,4-thiazine-4-yl)sydnonimine, 3-(3,3-dimethyl-1,1-dioxo-1,4-thiazine-4-yl)sydnonimine, 3-(3,3-dimethyl-1,4-thiazine-4-yl)sydnonimine, 3-(cis-2,6-dimethylpiperidino)sydnonimine, 3-morpholinosydnoniminechloride (Linsidomine; SIN-1), 3-(cis-2,6-dimethylpiperidino)-N-(4-methoxybenzoyl)sydnonimine (Pirsidomin) and N-ethoxycarbonyl-3-morpholinosydnonimine (Molsidomine).

As used in the specification and appended claims the following terms have the meaning indicated:

Each $R^5$ is independently hydrogen, alkyl or aralkyl. Each $R^6$ is straight or branched alkene chain optionally substituted by hydroxy, mercapto, alkylthio, aryl, cycloalkyl, —N(R$^4$)$_2$, —C(O)OR$^4$ or —C(O)N(R$^4$)$_2$. Each $R^7$ is independently hydrogen, alkyl or aralkyl.

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, the alkyl radical may be optionally substituted by hydroxy, alkoxy, aryloxy, haloalkoxy, cyano, nitro, mercapto, alkylthio, cycloalkyl, —N(R$^4$)$_2$, —C(O)OR$^4$, —C(O)N(R$^4$)$_2$ or —N(R$^4$)—C(O)—R$^4$ where each R$^4$ is as defined in the Summary of the Invention. Unless stated otherwise specifically in the specification, it is understood that for radicals, as defined below, that contain a substituted alkyl group that the substitution can occur on any carbon of the alkyl group.

"Alkoxy" refers to a radical of the formula —OR$_a$ where R$_a$ is an alkyl radical as defined above, e.g., methoxy, ethoxy, n-propoxy, 1-methylethoxy (iso-propoxy), n-butoxy, n-pentoxy, 1,1-dimethylethoxy (t-butoxy), and the like. Unless stated otherwise specifically in the specification, it is understood that for radicals, as defined below, that contain a substituted alkoxy group that the substitution can occur on any carbon of the alkoxy group. The alkyl radical in the alkoxy radical may be optionally substituted as described above.

"Alkylthio" refers to a radical of the formula —SR$_a$ where R$_a$ is an alkyl radical as defined above, e.g., methylthio, ethylthio, n-propylthio, 1-methylethylthio (iso-propylthio), n-butylthio, n-pentylthio, 1,1-dimethylethylthio (t-butylthio), and the like. Unless stated otherwise specifically in the specification, it is understood that for radicals, as defined below, that contain a substituted alkylthio group that the substitution can occur on any carbon of the alkylthio group. The alkyl radical in the alkylthio radical may be optionally substituted as described above.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical may be optionally substituted by hydroxy, alkoxy, haloalkoxy, cyano, nitro, mercapto, alkylthio, cycloalkyl, —N(R$^4$)$_2$, —C(O)OR$^4$, —C(O)N(R$^4$)$_2$ or —N(R$^4$)—C(O)—R$^4$ where each R$^4$ is as defined in the Summary of the Invention. Unless stated otherwise specifically in the specification, it is understood that for radicals, as defined below, that contain a substituted alkenyl group that the substitution can occur on any carbon of the alkenyl group.

"Alkynyl" refers to a straight or branched monovalent hydrocarbon chain radical consisting solely of carbon and hydrogen atoms, containing at least one triple bond, having from two to eight carbon atoms, and which is attached to the rest of the molecule by a single bond, e.g., ethynyl, prop-1-ynyl, but-1-ynyl, pent-1-ynyl, pent-3-ynyl, and the like. Unless stated otherwise specifically in the specification, the alkynyl radical may be optionally substituted by hydroxy, alkoxy, haloalkoxy, cyano, nitro, mercapto, alkylthio, cycloalkyl, —N(R$^4$)$_2$, —C(O)OR$^4$, —C(O)N(R$^4$)$_2$ or —N(R$^4$)—C(O)—R$^4$ where each R$^4$ is as defined in the Summary of the Invention. Unless stated otherwise specifically in the specification, it is understood that for radicals, as defined below, that contain a substituted alkynyl group that the substitution can occur on any carbon of the alkynyl group.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of alkyl, halo, nitro, cyano, haloalkyl, haloalkoxy, mercapto, alkylthio, phenyl, cycloalkyl, —OR$^4$ (including hydroxy and alkoxy), —N(R$^4$)$_2$, —R$^6$—N(R$^4$)$_2$, —N(R$^4$)—C(O)OR$^7$, —R$^6$—N(R$^4$)—C(O)OR$^7$, —N(R$^4$)—C(O)—R$^4$, —R$^6$—N(R$^4$)—C(O)—R$^4$, —C(O)OR$^4$, —R$^6$—C(O)OR$^4$, —C(O)—N(R$^4$)$_2$, —R$^6$—C(O)—N(R$^4$)$_2$, —C(O)—R$^6$—N(R$^4$)$_2$, —N(R$^5$)—C(NR$^5$)—N(R$^5$)$_2$, —N(R$^5$)—C(O)—N(R$^4$)$_2$ and —N(R$^5$)—C(O)—R$^6$—N(R$^4$)$_2$ where each R$^4$, R$^5$, and R$^6$ are as defined above in the Summary of the Invention.

"Aralkyl" refers to a radical of the formula —R$_a$R$_b$ where R$_a$ is an alkyl radical as defined above and R$_b$ is one or more aryl radicals as defined above, e.g., benzyl, diphenylmethyl and the like. The aryl radical(s) may be optionally substituted as described above.

"Aralkoxy" refers to a radical of the formula —OR$_d$ where R$_d$ is an aralkyl radical as defined above, e.g., benzyloxy, and the like. The aryl radical may be optionally substituted as described above.

"Aralkenyl" refers to a radical of the formula —R$_c$R$_b$ where R$_c$ is an alkenyl radical as defined above and R is one or more aryl radicals as defined above, e.g., 3-phenylprop-1-enyl, and the like. The aryl radical(s) and the alkenyl radical may be optionally substituted as described above.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like. The alkylene chain may be optionally substituted by one or more substituents selected from the group consisting of aryl, halo, hydroxy, alkoxy, haloalkoxy, cyano, nitro, mercapto, alkylthio, cycloalkyl, —N(R$^4$)$_2$, —C(O)OR$^4$, —C(O)N(R$^4$)$_2$ or —N(R$^4$)—C(O)—R$^4$ where each R$^4$ is as described above in the Summary of the Invention. The alkylene chain may be attached to the rest of the molecule through any two carbons within the chain.

"Alkenylene chain" refers to a straight or branched divalent hydrocarbon chain consisting solely of carbon and hydrogen, containing at least one double bond and having from two to eight carbon atoms, e.g., ethenylene, prop-1-enylene, but-1-enylene, pent-1-enylene, hexa-1,4-dienylene, and the like. The alkenylene chain may be optionally substituted by one or more substituents selected from the group consisting of aryl, halo, hydroxy, alkoxy, haloalkoxy, cyano, nitro, mercapto, alkylthio, cycloalkyl, —N(R$^4$)$_2$, —C(O)OR$^4$, —C(O)N(R$^4$)$_2$ or —N(R$^4$)—C(O)—R$^4$ where each R$^4$ is as described above in the Summary of the Invention. The alkenylene chain may be attached to the rest of the molecule through any two carbons within the chain.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, aryl, aralkyl, halo, haloalkyl, hydroxy, alkoxy, haloalkoxy, cyano, nitro, mercapto, alkylthio, cycloalkyl, —N(R$^4$)$_2$, —C(O)OR$^4$, —C(O)N(R$^4$)$_2$ or —N(R$^4$)—C(O)—R$^4$ where each R$^4$ is as defined in the Summary of the Invention.

"Cycloalkylene" refers to a stable divalent monocyclic or bicyclic hydrocarbon consisting solely of carbon and hydrogen atoms, having from three to ten carbon atoms, and which is saturated and attached to the rest of the molecule by two single bonds, e.g., cyclopropylene, cyclobutylene, cyclopentylene, cyclohexylene, decalinylene and the like. Unless otherwise stated specifically in the specification, the term "cycloalkylene" is meant to include cycloalkylene moieties which are optionally substituted by one or more substituents independently selected from the group consisting of alkyl, aryl, aralkyl, halo, haloalkyl, hydroxy, alkoxy, haloalkoxy, cyano, nitro, mercapto, alkylthio, cycloalkyl, —N(R$^4$)$_2$, —C(O)OR$^4$, —C(O)N(R$^4$)$_2$ or —N(R$^4$)—C(O)—R$^4$ where each R$^4$ is as defined in the Summary of the Invention.

"N-heterocyclyl" refers to a stable 3- to 15-membered ring radical which consists of carbon atoms and from one to five heteroatoms selected from the group consisting of nitrogen, oxygen and sulfur wherein at least one of the heteroatoms is a nitrogen. For the purposes of this invention, the N-heterocyclyl radical may be a monocyclic, bicyclic or a tricyclic ring system, which may include fused or bridged ring systems; and the nitrogen, carbon or sulfur atoms in the N-heterocyclyl radical may be optionally oxidized; the nitrogen atom may be optionally quaternized; and the N-heterocyclyl radical may be partially or fully saturated or aromatic. The N-heterocyclyl radical may be attached to the main structure at any heteroatom or carbon atom which results in the creation of a stable compound. Examples of such N-heterocyclyl radicals include, but are not limited to, azepinyl, azetidinyl, benzimidazolyl, benzoxazolyl, carbazolyl, decahydroisoquinolyl, quinuclidinyl, imidazolyl, imidazolinyl, imidazolidinyl, isothiazolidinyl, indolyl, isoindolyl, indolinyl, isoindolinyl, indolizinyl, isoxazolyl, isoxazolidinyl, morpholinyl, benzothiadiazolyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, perhydroazepinyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydroisoquinolyl, thiomorpholinyl, thiomorpholinyl sulfoxide, and thiomorpholinyl sulfone. The carbon atoms in the N-heterocyclyl radical may be optionally substituted by alkyl, halo, nitro, cyano, haloalkyl, haloalkoxy, mercapto, alkylthio, phenyl, cycloalkyl, —$OR^4$, —$N(R^4)_2$, —$R^6$—$N(R^4)_2$, —$N(R^4)$—$C(O)OR^7$, —$R^6$—$N(R^4)$—$C(O)OR^7$, —$N(R^4)$—$C(O)$—$R^4$, —$R^6$—$N(R^4)$—$C(O)$—$R^4$, —$C(O)OR^4$, —$R^6$—$C(O)OR^4$, —$C(O)$—$N(R^4)_2$, —$R^6$—$C(O)$—$N(R^4)_2$, —$C(O)$—$R^6$—$N(R^4)_2$, —$N(R^5)$—$C(NR^5)$—$N(R^5)_2$, —$N(R^5)$—$C(O)$—$N(R^4)_2$ and —$N(R^5)$—$C(O)$—$R^6$—$N(R^4)_2$ where each $R^4$, $R^5$, $R^6$ and $R^7$ are as defined above in the Summary of the Invention. The nitrogen atoms in the N-heterocyclyl may be optionally substituted by —$C(NR^5)$—$N(R^5)_2$, —$C(NR^5)$—$R^4$, —$C(O)$—$N(R^4)_2$ or —$C(O)$—$R^6$—$N(R^4)_2$ where each $R^4$, $R^5$ and $R^6$ and $R^7$ are as defined above.

Preferred N-heterocyclyl radicals are piperidinyl, tetrahydrosoquinolinyl, or benzothiadiazolyl. "Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —$OR_c$ where $R_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Prevention" includes that NO deficiency induced disturbances of the cerebral microcirculation may be avoided before they occur. For example, a NO donor may be applied to a patient prior to brain surgery or any other potential irritation of the brain surface that may cause an NO deficiency induced disturbance of the cerebral microcirculation as described herein.

In the present invention, the terms "cerebral vasospasm" and "cerebrovascular spasm" are used interchangeably. Thus, herein "CVS" is an abbreviation for both said terms.

In various embodiments of the present invention, the term "treatment, prevention and/or amelioration" is to be read as "at least one of treatment, prevention and a melioration".

The National Institutes of Health stroke scale (NIH-SS) is a graded neurological examination that assesses speech, language cognition, inattention, visual field abnormalities, motor and sensory impairments, and ataxia. The scale was developed for use in acute-stroke therapy trials and has since been widely used as a standard part of the assessment in clinical trials. This scale, along with many others, has been evaluated in its clinical usefulness in the assessment of the stroke patient. The NIH-SS permits a high-resolution evaluation of a patient's neurological status. To obtain the finding on the NIH-SS, various neurological aspects are investigated and assigned point scores. The total point score is a measure of the severity of the symptoms of stroke, the point score increasing with the severity of the symptoms. This rating scale is also suitable for monitoring the course of the symptoms after stroke and for quantifying the success of any treatment used. In general, it is possible to establish a correlation between the size of the infarct and the severity of the stroke as quantified by the stroke scale. Hence, the course of the size of the infarct under treatment is also suitable for the assessment of a treatment effect.

Rating scales such as the NIH-SS or the modified Rankin scale are generally used for the quantitative evaluation of the severity of a cerebral disorder, whether acute or under treatment. TCD (trans-cranial doppler) is a diagnostic procedure using ultrasound waves to measure blood flow through the major blood vessels of the brain. In particular, the purpose of this test is to detect any narrowing or blockage in arteries located at the base of the brain that may decrease or stop the flow of blood to the brain and increase blood flow velocities according to narrowed vessel diameter. The test is most useful at detecting decreased blood flow through narrow areas inside blood vessels. TCDs are especially useful for monitoring blood flow in the brain of stroke patients who are affected by brain swelling and vasospasm (which are cerebral blood vessel spasms).

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

FIGURES

FIG. 1: CT scan (modified Fisher grade IV SAH) with the blood filling basal and the right MCA subarachnoid cisterns as well as both frontal horns of lateral ventricules.

Figure 2:
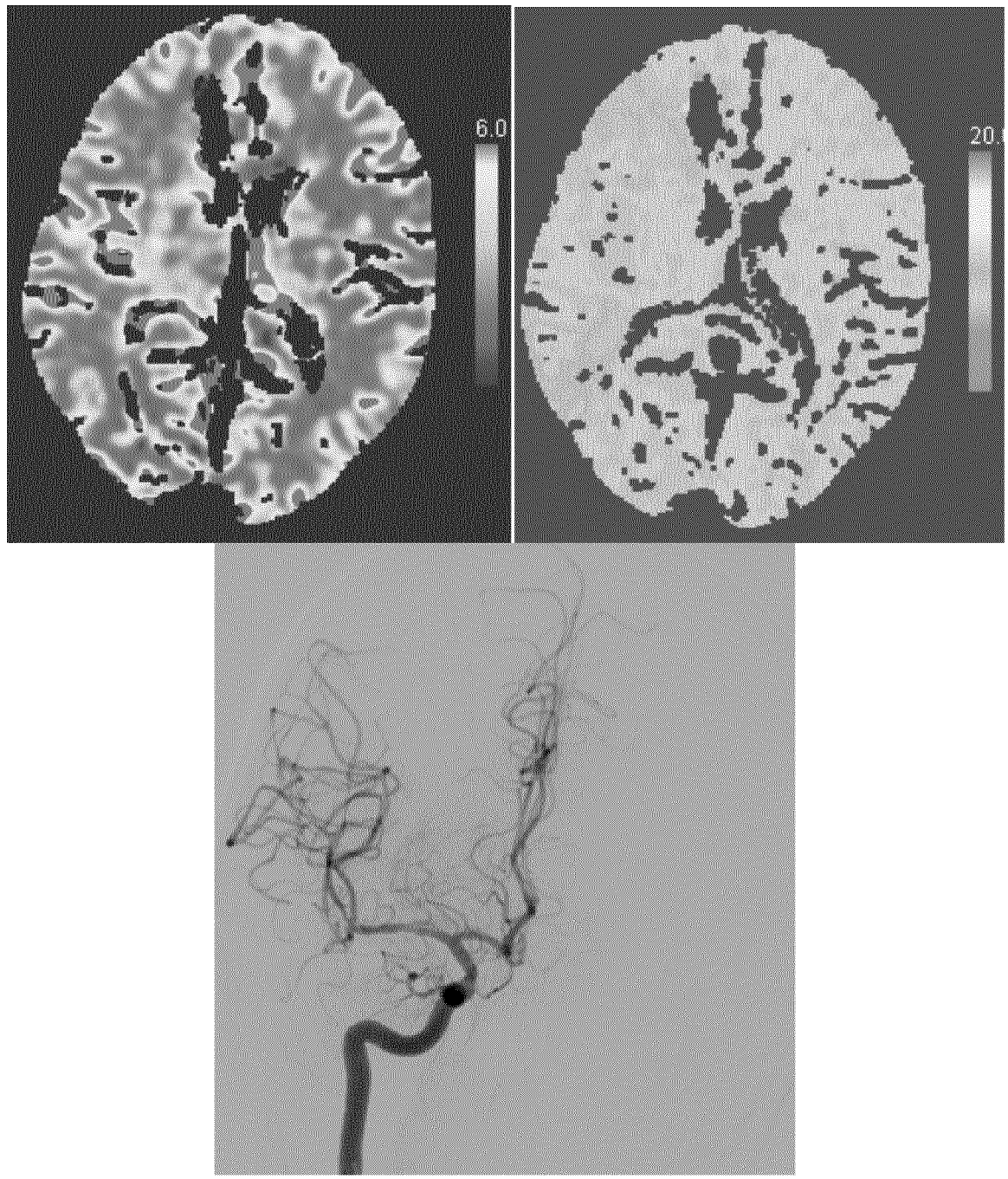

FIG. 2: Cerebral arteriographies were performed within ninety minutes after its intraventricular administration, which revealed no relevant vasospasm in any of the cerebral arteries; the cerebral transit time (CTT) was within normal limits.

Figure 3:

FIG. 3: Arteriography performed on the 17th day of ICU treatment revealed a local spasm with 90% reduction of the MCA in the direct vicinity of the coiled aneurysm; CTT remained normal.

Figure 4:
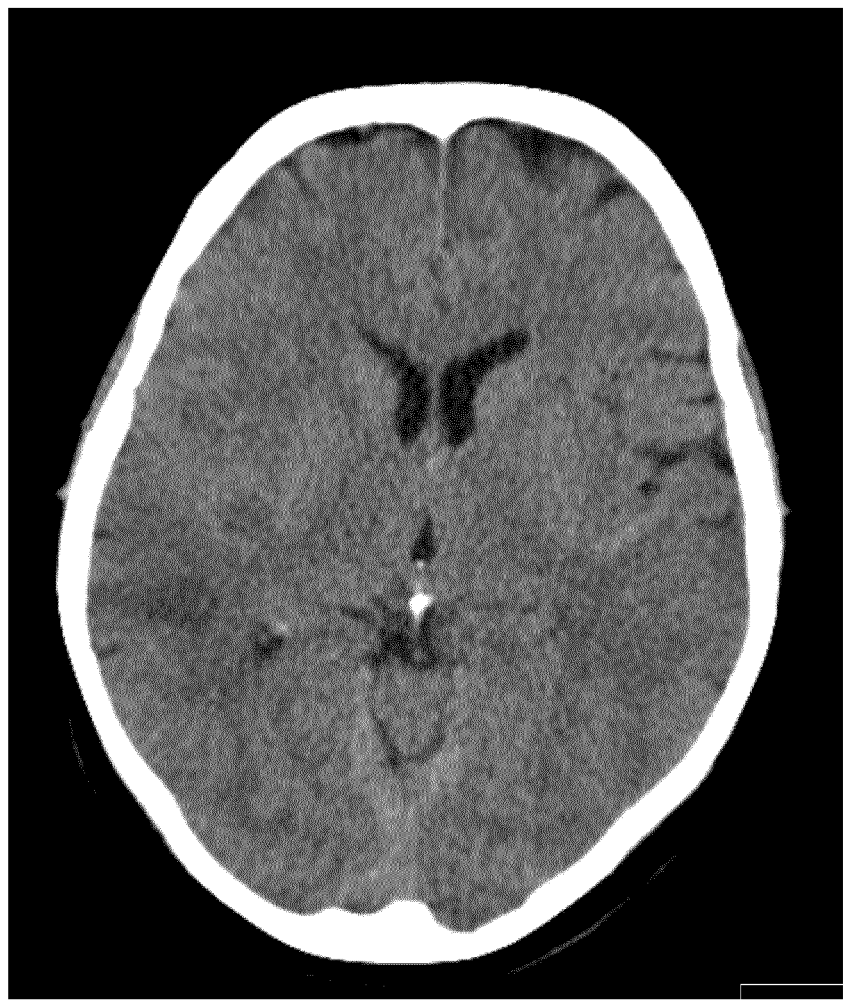

FIG. 4: Control CT scan revealed a minor right temporal ischemia.

EXAMPLES

The patient and her relatives provided an informed consent. Within 1 hour after experiencing "the worst headache of her life" a 65 years old German woman with no previous medical history was presented in the emergency room. The headache was accompanied by severe neck pain and vomiting. At admission her vital signs were within normal limits except a high blood pressure 175/95 mmHg, probably due to pain. Neurological examination revealed significant neck stiffness, progressive somnolence and the left sided hemidysaesthesia with no motor deficits. Her routine laboratory results were within normal limits. As the clinical course suggested (Hunt&Hess grade III, WFNS grade III) a subarachnoid hemorrhage was suspected and confirmed by CT scan (modified Fisher grade IV SAH 1 (FIG. 1)).

With the working diagnosis of a SAH from a ruptured intracranial aneurysm, the patient was admitted to the Neurosurgical Department and a right-sided external ventricular drainage (EVD) was immediately placed (Neuromedex ventriguard 10-French antibiotic augmented catheter and drainage system, Switzerland). Digitalized arteriography revealed an intracranial aneurysm of the right middle cerebral artery trifurcation (RMCA) with 50% diameter reduction of the M1 portion of the right MCA (M1). The aneurysm was coiled with 2 coils (2 mm/4 cm Target Softcoils, Stryker) within 5 hours after admission (6 hours after SAH) and the patient was admitted to a Neurosurgical ICU. Because of the high risk of further clinical deterioration, she was placed on the following SAH protocol:

(1) Continuous monitoring of blood pressure, pulsoxymetry, heart rate, breathing rate, and BIS (Bispectral index) recording.

(2) Hourly report on ICP, pupil reactions, GCS scale, fluid balance, and, in intubated patients, continuous NIRS measurement, routine blood gases every 4 hours, laboratory control and TCD at least once a day. Extubation is performed as soon as it is safe.

(3) Nimodipine is preferably administered orally 6×60 mg or 1-2 mg/h intravenously. Goals are a normotension (MAP>60-<100), an euvolemia, balanced laboratory parameters, hemoglobin content between 9-11 g/dl, a normothermia. In case of low output hypotension due to SAH nimodipine dosage adapt to vasopressor demand.

(4) Routine CCT controls are preformed after interventions, additional CCT on demand just as CT perfusion and digitalized angiography.

(5) In case of serious delayed cerebral vasospasm an emergency protocol is used (TCD mean flow in the anterior circulation >140 cm/sec or in posterior circulation >120 cm/sec, Lindegaard-Index >3 and/or in CT perfusion proven disturbances like a prolonged CTT). This "rescue" protocol contains an induction of a slight systemic hypertension (MAP 90-100 mmHg) and an intravenous administration of Molsidomine in escalating dosages. 3H-therapy is not used routinely. A systemic hypertension (MAP>100 mmHg) is in most cases achieved with vasopressors (0.1-0.2 µg/hr noradrenaline) and it is used unless hemorrhagic transformations in parenchyma are detected. In persisting vasospasm or developing DCI we carry on with either intrathecally administered SNP and/or selective intraarterial nimodipine with or without angioplasty. For all of these treatments a written consent of patients or next of kin is obtained.

and an anti-vasospastic was started, which included Nimodipine (Bayer, Germany; 6×60 mg or 1-2 mg/hr intravenously), normotension (MAP>60-<90 mmHg), euvolemia and drainage of CSF when ICP was above 20 mmHg. Within several hours after starting the treatment and after drainage of 80 ml of CSF the patient's clinical status improved, focal neurological signs resolved (Hunt&Hess and WFNS grades I-II). Nevertheless, the presence and further progression of a significant vasospasm was confirmed with an increase of mean blood flow velocity in the right MCA from 130 cm/sec to 160-190 cm/s on the 2nd day after SAH. The patient's clinical status slightly deteriorated with increased fatigue and headache, but still without focal deficits (HH II; WFNS II, GCS 14).

The MAP was held about 80-90 mmHg using crystalloids and initially due to short-term hypotension evoked by acute SAH up to 0.9 mg/hr noradrenaline (Sanofi-Aventis, Germany) were needed. Any fluid and sodium losses (range 121 to 142 mEq/ml) were replaced. However, despite all those efforts, high TCD values remained unchanged and her consciousness fluctuated. In order to avoid brain ischemia, the treatment was expanded by addition of Molsidomine (Therabel, Belgium, 20 mg ampoules) as a rescue protocol in nimodipine resistant vasospasm based on the present inventor's experience (Ehlert, loc. cit.).

The continuous intravenous infusion of Molsidomine was started after obtaining a written consent regarding combined NO donor therapy on day 2 after SAH. Within 72 hr the dose gradually increased from initially 1.7 mg/hr to 16 mg/hr under a careful monitoring of all vital signs without additional vasopressors.

During intravenous Molsidomine at the full dose the mean blood flow velocities in both MCAs did not exceed 160 cm/sec and with a GCS of 14-15 the patient remained clinically stable (HH I, WFNS I) for several days. But on the morning of the 9th day after SAH she had a sudden onset of a right-sided hemiplegia with global aphasia with an increased somnolence (HH IV; WFNS IV, GCS 8). At that time TCD showed a insignificant increase of mean flow velocities from 140 cm/sec the day before to 150 cm/sec in the left MCA (LMCA) and unchanged velocities (80 cm/sec) in the RMCA. To address this clinical deterioration most likely evoked by a spasm of the LMCA, an intraventricular bolus of the spontaneous NO donor sodium nitroprusside (SNP, Nitroprussiat Fides, Rottapharm, Spain) was administered additionally to continuous and ongoing Nimodipine and Molsidomine therapy.

Initially, a rescue dose of 3 mg of SNP was infused through EVD at the bedside which evoked (1) an immediate and considerable increase of the systemic blood pressure MAP from 80 mmHg to 120 mm Hg, that was controlled with Urapidil (fractionated dose of 200 mg; MAP decreased to 95 mmHg); (2) emesis that was treated by Zofran (Ondansetron, GlaxoSmithKline, Germany) and (3) a short-term increase of the ICP for about three minutes from 11 mm Hg to 23 mm Hg, that was treated with evacuation of 5 ml of CSF.

After those interventions the MAP remained slightly higher at 100 mmHg but ICP-values returned to normal (2-5 mm Hg). A perfusion CT scan after SNP administration did not reveal any pathological findings. One hour later the patient was completely vigilant without focal deficit (Hunt&Hess grade I, WFNS I, GCS 15). Despite a mild hypertension (MAP at 90 mmHg), mean blood flow velocities declined by 30 cm/sec in both MCAs to 130 cm/sec at the LMCA and to 50 cm/sec at the RMCA.

Unfortunately, 8 hours later the patient's clinical status deteriorated again. She developed a left-sided hemiplegia and neglect with increasing somnolence (Hunt&Hess grade IV, WFNS IV, GCS 8). The mean velocity in the right MCA increased to 170-190 cm/sec. Since the first dose of SNP had evoked a short lasting increase of ICP, this time we removed 5 ml CSF before the SNP administration. The second dose of intrathecal SNP (3 mg) was administered without any rise of ICP and the patient recovered completely within 45 min (HH I, WFNS I, GCS 15) after SNP. Urapidil controlled a corresponding increase of MAP after SNP. On the 10th day after SAH she developed the 3rd episode of DCI that was treated with 5 mg SNP (due to quickly relapsing DCI). Cerebral arteriographies were performed within ninety minutes after its intraventricular administration, which revealed no relevant vasospasm in any of the cerebral arteries (FIG. 2); the cerebral transit time (CTT) was within normal limits.

The patient recovered and remained stable (Hunt&Hess grade I, WFNS I and GCS 15) for several days. The daily drainage of CSF was stopped and the ventricular catheter was removed on day 14 after SAH. Unfortunately, on day 17th after SAH the patient developed another DCI with left-sided hemiplegia and right-sided hemiparesis, she became comatose and required intubation (Hunt&Hess grade IV, WFNS IV, GCS 8). The mean flow velocities in both MCAs were above 170 cm/sec. A perfusion CCT revealed a reduced perfusion in the posterior, media- and anterior-vascular territories more pronounced on the right than on the left side. CCT did not show any infarctions. In OR a ventricular drainage was re-established to control ICP and the 4th dose (3 mg) of SNP was administered with Near Infrared Spectroscopy (NIRS) monitoring (Covidien). O$_2$ saturation (as rSO$_2$%) gradually increased on the right and left side, from 55% and 57% to 73% and 80% respectively within 5 min after SNP administration. Also, within minutes after SNP administration, the patient started to move both sides and was extubated. However, 1 hr later a DCI recurred and required re-intubation and repeated intrathecal administration of 5 mg of SNP (5th time) with the side effects treated as before. Patient again started to move all extremities but remained somnolent. Another arteriography was performed on the 17th day of ICU treatment and revealed a local spasm with 90% reduction of the MCA in the direct vicinity of the coiled aneurysm (FIG. 3); but CTT remained normal. An intraarterial infusion of Nimodipine was ineffective; so, again 3 mg of SNP was administered intraventricularly. Within 15 hr after the 6th SNP administration, the patient's clinical status dramatically improved again and she was extubated (Hunt&Hess grade I, WFNS I, GCS 15). A control CT scan revealed a minor right temporal ischemia (FIG. 4). A last episode of DCI led to the 7th application of SNP.

In summary, despite Nimodipine and Molsidomine infusions recurrent clinical deteriorations were observed 7 times (right- and left-sided deficits or coma). Each of them was accompanied with high mean blood flow velocities (170-190 cm/sec) in the vessels corresponding to neurological deficit or in both MCAs. Each deterioration was treated with intraventricular SNP-bolus (3 or 5 mg), inducing a systemic blood pressure increase controlled by Urapidil but without ICP increases above 15 mmHg. Each DCI resolved completely and mean blood low velocities in the MCAs decreased to 100-148 cm/sec. A brain MRI revealed the known small right-sided temporal ischemia. The EVD was removed (at the 22 nd day) and the patient was completely mobilized on the 30th day after SAH.

Nimodipine- and Molsidomine-treatments were tapered over the next several days. On the 38th day after SAH she was discharged to a rehabilitation center in a good clinical status (Hunt&Hess grade 0 and WFNS grade I, mNIH-SS and mRS grades 0) without cognitive deficit. On follow-up visits at 3, 6, and 12 months the patient got back her mental, physical, and neurological status as before the SAH. At 6 months, the brain MRI revealed the known lesion and a glial defect in the trail of the EVD; MR-angiography did not reveal any evidence of reperfusion of the aneurysm.

The patient had most early *stigmata* predicting a poor outcome (Baldwin et al., *Stroke*. 2004; 35:2506-2511) and therefore an extremely poor prognosis which required an aggressive and bold decision from the medical team, the patient and her family. Based on many years of pre- (Pluta et al., *JAMA*. 2005; 293:1477-1484) and clinical research (Pluta et al., *PLoS One*. 2011; 6:e14504; Oldfield et al., *J Neurosurg*. 2013; 119:634-641), which pointed toward a decreased availability of NO in the vessels and surrounding brain after SAH as well as the present inventor's recent experience (Ehlert at al., loc. cit.), it was decided early to use Molsidomine in this patient. Using this protocol the present inventor had reported a significant improvement of the outcome in the NIH-SS and mRS and a decrease of the rate of vasospasm-associated infarcts. The basic concept was that after an aneurismal SAH a NO sink-effect occurs in response to hemoglobin breakdown evoking vasoconstriction and decreased CBF.

This rationale led to an intravenous NO replacement by Molsidomine that releases after passage through the liver the spontaneous NO-donor SIN-1. However, spasm-associated brain ischemias (DCI) developed in the patient despite of Molsidomine. This was also observed in several patients who had cerebral infarcts in the previous study (Ehlert et al., loc. cit.). Accordingly, the present inventor used in addition an active NO-delivering NO donor, particularly SNP with the aim of overcoming possible shortcomings of a NO-donor which has to be metabolized. The rationale was to resolve developing DCI using a local NO boost at the bedside setting prior to development of irreversible ischemia. Each bolus of a local NO boost reversed vasospasm-related clinical deterioration without a rise of met-hemoglobin in blood gases or clinical signs of cyanide poisoning.

To this end, despite severe complications of aneurismal SAH that usually result in a poor outcome, the clinical outcome of this patient was excellent. At 3, 6, and 12 months follow up her mNIH-SS and mRS were 0 and the patient did not have any cognitive deficit.

TABLE 1

Summary of clinical events, therapeutic and diagnostic interventions during continuously infused Molsidomine

| POD# | SYMPTOMS | SNP ITH. | MCA TCD R/L PRE | MCA TCD R/L POST | MAP | RADIOLOGY | RESULT |
|---|---|---|---|---|---|---|---|
| 0-2 | PROGRESSIVE FATIGUE; HEADACHE | N.A. | right MCA from 130 to 160-190 | N.A. | 90 | 50% SPASM OF RIGHT MCA/M1 | N.A. |
| $9^{th}$ (first episode) | R hemiplegia, aphasia | 3 mg ($1^{st\ dose}$) | r: 160/ l: 150 | r: 134/ l: 120 | 130* | post SNP: 2,3 (CT-A, CT-P) no pathologies | complete recovery |
| $9^{th}$ (second episode) | hemiplegia l, sopor | 3 mg ($2^{nd\ dose}$) | r: 190 | r: 148 | 105* | None | complete recovery |
| $10^{th}$ (3rd episode) | hemiplegia l, sopor | 5 mg ($3^{rd\ dose}$) | r: 170 | r: 107 | 94* | post SNP: 1,4 (CT, DSA) no pathologies, normal CT scan | full recovery, later on changing vigilance |
| $17^{th}$ (4th episode) | hemiplegia r hemiparesis l, sopor, Intubation | 3 mg ($4^{th\ dose}$) | R: 170 L: 120 | R: 140 L: 105 | 103* | pre SNP: 1,2,3 (CT; CT-A; CT-P) impaired perfusion both sides l > r, CTT prolonged, high grade vasospasm in MCAs and ACA | full recovery, extubation |
| $17^{th}$ (5th episode) | hemiparesis l, relapsed sopor | 3 mg ($5^{th\ dose}$) | Emergency n.a. | R: 95 L: 80 | 105* | 1,4 post SNP: local high grade vasospasm at coil, normal CTT, no reaction to nimodipine. No infarction | Re-intubation |
| 18 ($6^{th}$ episode) | n.a.: still intubated | 3 mg ($6^{th\ dose}$) | R: 160 L: 110 | n.a. | 105* | 1: very small cortical infarction in right temporal lobe | extubation, full recovery |
| 22 ($7^{th}$ episode) | sudden loss of vigilance | 3 mg ($7^{th\ dose}$) | R: 180 L: 140 | R: 120 L: 100 | 110* | Not done due to recovery. | full recovery |

TABLE 1-continued

Summary of clinical events, therapeutic and diagnostic interventions during continuously infused Molsidomine

| POD# | SYMPTOMS | SNP ITH. | MCA TCD R/L PRE | MCA TCD R/L POST | MAP | RADIOLOGY | RESULT |
|---|---|---|---|---|---|---|---|
| 23-38 | Tapering of Molsidomine and Nimodipine | | Normal values | Normal values | n.s. | MRI (5): tiny temporal ischemic lesion and gliosis at ventricular drainage site | Mobilization, Discharge at 38th POD mRS: 0 mNIH-SS: 0 full cognitive skills |

(POD#: post operative day,
R: right,
L: left,
MCA: middle cerebral artery, flow in cm/sec, all values mean,
*use of Urapidil,
CT (1): cranial computed tomography,
CT-A (2): CT-angiography,
CT-P (3): CT-Perfusion scans
DSA (4): Digitalized Substraction Angiography (4),
MRI (5): Magnetic Resonance Imaging,
SNP: sodium nitroprusside,
CTT: cerebral transit time, Molsidomine was tapered 1.6 mg per day under TCD control, Nimodipine was reduced 60 mg every two days.

The invention claimed is:

1. A method of treatment, prevention and/or amelioration of disturbances of the cerebral macro- and microcirculation which disturbances cause cerebrovascular spasms (CVS) and/or malperfusion of brain parenchyma caused by blood vessel and blood flow dysregulation, said method comprising administering to the subject a NO donor prodrug which has to be metabolized by said subject into the active NO-delivering form and intraventricularly administering an active NO-delivering NO donor, wherein said active NO-delivering NO donor is nitroprusside, wherein said NO donor prodrug is administered intravenously, and wherein said NO donor prodrug is N-ethoxycarbonyl-3-morpholinosydnonimine (molsidomine), wherein intraventricularly administered nitroprusside acts synergistically with intravenously administered molsidomine by reducing cerebrovascular spasms and/or delayed cerebral ischemia (DCI) and wherein nitroprusside is administered at a dose in the range of 2 to 5 mg/hour and the molsidomine is administered at a dose in the range of 1 mg/hour to 16 mg/hour.

2. The method of claim 1, wherein said disturbances of the cerebral macro- and microcirculation are induced by nitric oxide deficiency.

3. The method of claim 1, wherein the NO donor prodrug has the formula II

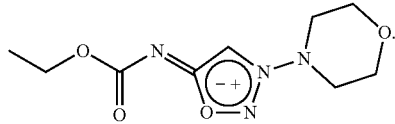

4. The method of claim 1, wherein said method further comprises administering Nimodipine and/or Clazosentan.

5. The method of claim 1, wherein the cerebrovascular spasms cause secondary neurological deficiencies (DIND) and/or brain infarction.

6. The method of claim 1, wherein the NO deficiency-induced disturbances are due to an intracranial hemorrhage or stroke.

7. The method of claim 1, wherein the intracranial hemorrhage results from a traumatic or a non-traumatic cause; wherein intracranial hemorrhage is an intra-axial hemorrhage (cerebral hemorrhage) or extra-axial hemorrhage;
wherein the intra-axial hemorrhage is an intraparenchymal hemorrhage, intraventricular hemorrhage, or intraventricular traumatic diffuse bleeding; or
wherein the intra-axial hemorrhage is caused by brain trauma, hemorrhagic stroke and/or spontaneous bleeding into the brain tissue.

8. The method of claim 1, wherein the extra-axial hemorrhage is extra-axial chronical response acute bleeding; wherein the extra-axial hemorrhage is an epidural, subdural or subarachnoid hemorrhage; or wherein the extra-axial hemorrhage is caused by an aneurysm or trauma.

9. The method of claim 1, wherein the subarachnoid hemorrhage is spontaneous or traumatic.

10. A dosage regime for use in a method of treatment, prevention and/or amelioration of disturbances of the cerebral macro- and microcirculation which disturbances cause cerebrovascular spasms (CVS) and/or malperfusion of brain parenchyma caused by blood vessel and blood flow dysregulation, comprising
(a) continuously administering a NO donor prodrug that is N-ethoxycarbonyl-3-morpholinosydnonimine (molsidomine) at a dose range from 1 mg/hour to 16 mg/hour, wherein the prodrug is administered intravenously prior to, concurrently and/or after NO deficiency-induced disturbances of the cerebral macro- and microcirculation such that the mean arterial pressure (MAP) is maintained at at least 65 mm Hg; and
(b) administering an active NO-delivering NO donor that is nitroprusside intraventricularly at a dose range of 2 mg/hour to 5 mg/hour.

11. A kit comprising Molsidomine and Nitroprusside, and instructions for treatment, prevention and/or amelioration of disturbances of the cerebral macro- and microcirculation which disturbances cause cerebrovascular spasms (CVS) and/or malperfusion of brain parenchyma caused by blood vessel and blood flow dysregulation, wherein Molsidomine is to be administered intravenously and Nitroprusside is to be administered intraventricularly, and optionally further comprising Nimodipine and/or Clazosentan.

12. The method of claim 1, wherein the NO donor prodrug is continuously administered to provide a permanent level of NO in the brain during administration of nitroprusside and molsidomine.

13. The method of claim 1, wherein intraventricular administration of nitroprusside in combination with intravenous administration of molsidomine eliminates occurrence of cerebrovascular spasms and/or DCI after administration.

14. The method of claim 1, wherein intraventricular administration of nitroprusside in combination with intravenous administration of molsidomine reduces secondary neurological deficiencies (DIND) and/or brain infarction.

15. The method of claim 1, wherein nitroprusside is administered at a dose of about 3 mg/hour.

16. The method of claim 1 wherein intraventricular administration of nitroprusside begins after initial intravenous administration of molsidomine.

17. The method of claim 1 wherein intraventricular administration of nitroprusside is provided in one or more bolus dose(s).

18. The method of claim 1 wherein intraventricular administration of nitroprusside does not cause a rise of met-hemoglobin in blood gases or clinical signs of cyanide poisoning.

* * * * *